(12) United States Patent
Ahn et al.

(10) Patent No.: US 10,941,268 B2
(45) Date of Patent: Mar. 9, 2021

(54) COSMETIC SUPPORTING STRUCTURE, METHOD FOR PREPARING SAME, AND COSMETIC COMPRISING SAME

(71) Applicant: KOLON INDUSTRIES, INC., Seoul (KR)

(72) Inventors: Tae-Hwan Ahn, Seoul (KR); Min-Ho Choi, Seoul (KR)

(73) Assignee: Kolon Industries, Inc., Seoul (KR)

( * ) Notice: Subject to any disclaimer, the term of this patent is extended or adjusted under 35 U.S.C. 154(b) by 44 days.

(21) Appl. No.: 15/780,455

(22) PCT Filed: Dec. 1, 2016

(86) PCT No.: PCT/KR2016/014077
§ 371 (c)(1),
(2) Date: May 31, 2018

(87) PCT Pub. No.: WO2017/095168
PCT Pub. Date: Jun. 8, 2017

(65) Prior Publication Data
US 2018/0362722 A1   Dec. 20, 2018

(30) Foreign Application Priority Data
Dec. 1, 2015 (KR) .......... 10-2015-0169858

(51) Int. Cl.
*C08J 9/36* (2006.01)
*A61Q 19/00* (2006.01)
(Continued)

(52) U.S. Cl.
CPC .............. *C08J 9/365* (2013.01); *A45D 34/04* (2013.01); *A61K 8/0266* (2013.01); *A61K 8/046* (2013.01); *A61K 8/86* (2013.01); *A61K 8/87* (2013.01); *A61K 8/891* (2013.01); *A61Q 17/005* (2013.01); *A61Q 17/04* (2013.01); *A61Q 19/00* (2013.01); *C08G 18/1833* (2013.01); *C08G 18/2027* (2013.01); *C08G 18/42* (2013.01);
(Continued)

(58) Field of Classification Search
CPC ........ C08J 9/365; C08J 9/125; C08J 2207/00; C08J 2375/06; C08J 2483/04; A61Q 19/00
See application file for complete search history.

(56) References Cited

U.S. PATENT DOCUMENTS 5,445,604 A    8/1995 Lang
9,492,370 B2   11/2016 Choi et al.
(Continued)

FOREIGN PATENT DOCUMENTS

EP    0417866 A1    3/1991
EP    1911368 A1    4/2008
(Continued)

OTHER PUBLICATIONS

European search report dated Sep. 13, 2018, in counterpart application EP 16871064.8. (10 pages).

*Primary Examiner* — Hai Vo
(74) *Attorney, Agent, or Firm* — Sughrue Mion, PLLC

(57) ABSTRACT

The present invention relates to a cosmetic-supporting structure, including a reticulated porous foam and a silicone coating layer, serving as an outer frame, on an outer surface of the foam, serving as an inner frame, a method of manufacturing the same, and a cosmetic product containing the same.

16 Claims, 1 Drawing Sheet

(51) Int. Cl.
| | |
|---|---|
| *A61K 8/891* | (2006.01) |
| *A61Q 17/04* | (2006.01) |
| *A61K 8/86* | (2006.01) |
| *A61K 8/87* | (2006.01) |
| *A61K 8/02* | (2006.01) |
| *A61Q 17/00* | (2006.01) |
| *A61K 8/04* | (2006.01) |
| *C08G 18/20* | (2006.01) |
| *C08G 18/18* | (2006.01) |
| *A45D 34/04* | (2006.01) |
| *C08G 18/42* | (2006.01) |
| *C08G 18/76* | (2006.01) |
| *C08J 9/12* | (2006.01) |
| *C08J 9/14* | (2006.01) |
| *C08G 101/00* | (2006.01) |

(52) U.S. Cl.
CPC .......... *C08G 18/7621* (2013.01); *C08J 9/125* (2013.01); *C08J 9/146* (2013.01); *A45D 2200/1018* (2013.01); *A45D 2200/1036* (2013.01); *A61K 2800/87* (2013.01); *C08G 2101/0008* (2013.01); *C08J 2203/10* (2013.01); *C08J 2203/144* (2013.01); *C08J 2203/182* (2013.01); *C08J 2205/044* (2013.01); *C08J 2207/00* (2013.01); *C08J 2375/06* (2013.01); *C08J 2483/04* (2013.01); *Y10T 428/249955* (2015.04); *Y10T 428/249958* (2015.04); *Y10T 428/249978* (2015.04)

(56) References Cited

U.S. PATENT DOCUMENTS

| | | | |
|---|---|---|---|
| 2006/0210612 A1* | 9/2006 | Simon | A61K 8/0208 424/443 |
| 2010/0286584 A1* | 11/2010 | Areskoug | C08G 18/4829 602/46 |
| 2011/0070423 A1 | 3/2011 | Jayakody et al. | |
| 2011/0111196 A1* | 5/2011 | Hubbs | B32B 38/08 428/220 |
| 2014/0023689 A1* | 1/2014 | Kim | A61Q 1/02 424/401 |
| 2014/0341959 A1 | 11/2014 | Choi et al. | |
| 2015/0313807 A1 | 11/2015 | Lynch et al. | |
| 2018/0015005 A1 | 1/2018 | Cho et al. | |

FOREIGN PATENT DOCUMENTS

| | | |
|---|---|---|
| EP | 3210590 A1 | 8/2017 |
| KR | 10-2011-0108672 A | 10/2011 |
| KR | 10-2013-0083852 A | 7/2013 |
| KR | 10-1385652 B1 | 5/2014 |
| KR | 10-2015-0063196 A | 6/2015 |
| KR | 10-1652756 B1 | 9/2016 |
| WO | 2004/094494 A2 | 11/2004 |

* cited by examiner

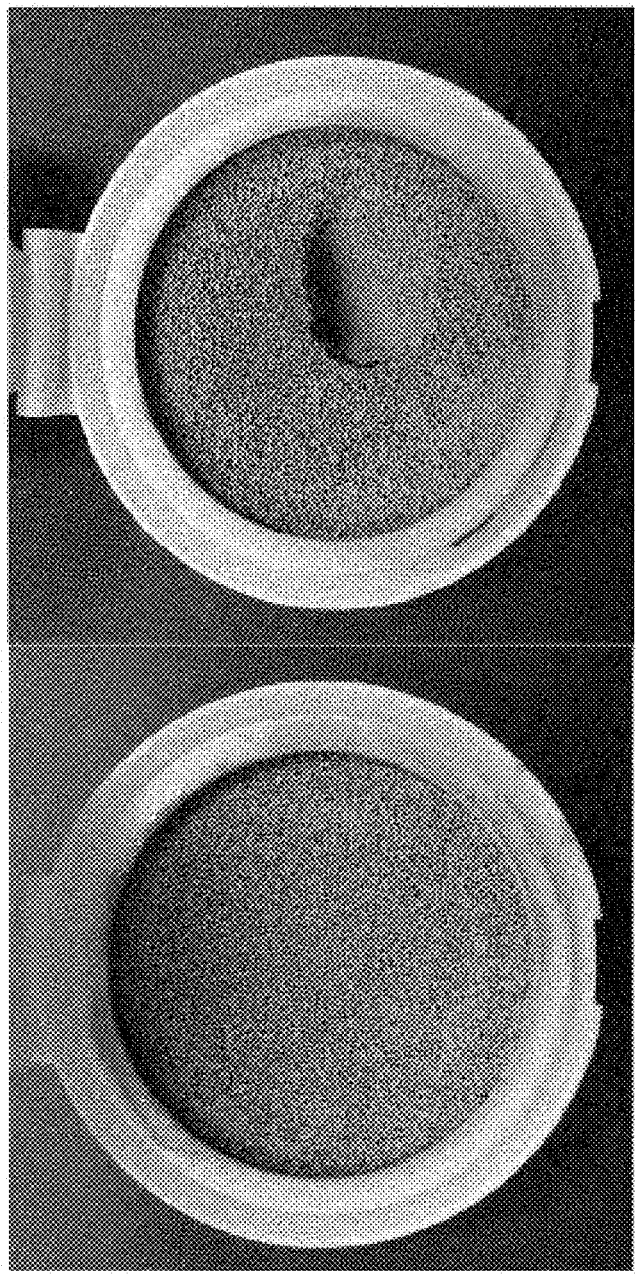

COSMETIC SUPPORTING STRUCTURE, METHOD FOR PREPARING SAME, AND COSMETIC COMPRISING SAME

TECHNICAL FIELD

The present invention relates to a cosmetic-supporting structure, a method of manufacturing the same, and a cosmetic product comprising the same.

BACKGROUND ART

Foam or sponge, which is porous, is capable of efficiently absorbing material, has elasticity and is capable of absorbing shocks, and is thus suitable for a variety of applications, including vehicles, industrial products such as electronics, living goods, and cosmetic products. The development of foam using new materials for various applications is required.

Foam for a cosmetic product is a kind of makeup tool for supporting a cosmetic or applying a cosmetic on the skin, and examples of the material therefor may include polyurethane, NBR, SBR, NR, BR, PVA, EVA, sponge, and the like. In recent years, the development of a material exhibiting chemical resistance, durability, and a pleasant sensation of use depending on a variety of formulations and applications of cosmetic products is further required.

Cosmetic compositions, which are typically charged in a vacuum container, a pump container or a glass container, are usually simply stored after being distributed. However, in accordance with recent lifestyle changes, leisure activities have become more popular and the frequency of use of cosmetic compositions increases even upon outdoor activities, and thus, the demand for a cosmetic composition, which is conveniently used and carried, is increasing.

In order to realize convenience of use and carrying of the cosmetic composition, the cosmetic composition is supported on sponge made of various materials, but it is not easy to find a material having superior durability, chemical resistance, color stability, charging capability, supporting capability and discharging capability.

Moreover, the properties of the conventional sponge are deteriorated by components of cosmetic compositions, such as a UV screen, an oil component (oil), a surfactant, an aqueous component, an emulsion stabilizer, an alcohol, etc., which undesirably deform the sponge.

Accordingly, there is a need to develop a material suitable for supporting a cosmetic composition, and research thereto is continuously ongoing.

CITATION LIST

Korean Patent Application Publication No. 10-2013-0083852

DISCLOSURE

Technical Problem

The present invention has been made keeping in mind the problems encountered in the related art, and the present invention is intended to provide a cosmetic-supporting structure, which exhibits superior durability, chemical resistance, color stability, elasticity and sensation of use, particularly superior deformation resistance and chemical resistance to a cosmetic composition, and a method of manufacturing the same.

In addition, the present invention is intended to provide a cosmetic product that includes the cosmetic-supporting structure having superior durability, chemical resistance, elasticity and sensation of use.

Technical Solution

Therefore, the present invention provides a cosmetic-supporting structure, comprising: a reticulated porous foam; and a silicone coating layer, serving as an outer frame, on the outer surface of the foam, serving as an inner frame.

In addition, the present invention provides a method of manufacturing a cosmetic-supporting structure, comprising: forming a silicone coating layer, serving as an outer frame, on the outer surface of a reticulated porous foam, serving as an inner frame.

In addition, the present invention provides a cosmetic product including the cosmetic-supporting structure.

Advantageous Effects

According to the present invention, a cosmetic-supporting structure is harmless to human bodies, and is superior in properties such as chemical resistance, shape retention, durability, color stability, elasticity, sensation of use, and the like. Also, when the cosmetic-supporting structure of the present invention is used to support a cosmetic, a cosmetic composition is well charged therein, and the cosmetic composition can be uniformly supported for a long period of time. Furthermore, the cosmetic composition can be discharged in an appropriate amount when necessary, and the sensation of use thereof can be improved. Thus, when the cosmetic-supporting structure according to the present invention is used, the cosmetic composition can be simply carried or used, and makeup can be conveniently applied during outdoor activities.

In particular, in the cosmetic-supporting structure according to the present invention, deformation resistance and chemical resistance to a cosmetic composition, including a UV screen and the like, which greatly affect the deformation of the cosmetic-supporting structure, can be effectively improved due to silicone coating.

BRIEF DESCRIPTION OF DRAWINGS

FIG. 1 show images of the foam shapes after storage of an ester-based polyurethane foam (Example 7, left) having a silicone coating layer and an ester-based polyurethane foam (Comparative Example 5, right) having no silicone coating layer, each of which is impregnated with a cosmetic, at 60° C. for 40 days.

BEST MODE

The present invention addresses a foam, configured such that a silicone resin is contained in a reticulated porous foam. In the present invention, the silicone resin is contained in the reticulated porous foam, thereby further improving properties such as durability, chemical resistance, color stability, elasticity and sensation of use.

Specifically, the present invention pertains to a cosmetic-supporting structure, comprising a reticulated porous foam and a silicone coating layer, serving as an outer frame, on the outer surface of the foam, serving as an inner frame.

The cosmetic-supporting structure of the present invention is a net-like structure configured to include an inner frame comprising the reticulated porous foam and an outer frame formed by covering the outer surface of the foam with a silicone resin. Accordingly, the portion thereof that comes into direct contact with the cosmetic is the silicone resin having superior chemical resistance and durability, whereby durability, chemical resistance, color stability, elasticity and sensation of use may be improved.

With the goal of manufacturing the cosmetic-supporting structure having the silicone coating layer, the thickness of the silicone coating layer, the weight ratio of the reticulated porous foam and the silicone coating layer, the pore size of the reticulated porous foam, the hardness of the reticulated porous foam, and the hardness of the silicone composition have to be selected within appropriate ranges in order to attain desired properties of the cosmetic-supporting structure and effects thereof, such as chemical resistance and the like.

In the cosmetic-supporting structure according to the present invention, the weight ratio of the reticulated porous foam and the silicone coating layer preferably falls in the range of 1:0.25 to 1:9, and more preferably 1:0.5 to 1:7. If the weight of the silicone coating layer is less than ¼ of the weight of the reticulated porous foam, improvements in chemical resistance to a cosmetic, durability, and deformation resistance may be reduced, which is undesirable. On the other hand, if the weight of the silicone coating layer exceeds 9 times the weight of the reticulated porous foam, it is difficult to attain appropriate hardness and pore size.

In the cosmetic-supporting structure according to the present invention, the thickness of the silicone coating layer preferably falls in the range of 1 μm to 100 μm, and more preferably 3 μm to 60 μm. If the thickness of the silicone coating layer is less than 1 μm, improvements in chemical resistance to a cosmetic, durability, and deformation resistance may become insignificant. On the other hand, if the thickness thereof exceeds 100 μm, it is difficult to attain appropriate hardness and pore size.

In the cosmetic-supporting structure according to the present invention, the pore size of the reticulated porous foam preferably falls in the range of 30 μm to 3,000 μm, and more preferably 100 μm to 1,000 μm. If the pore size of the foam is less than 30 μm, charging and discharging of the cosmetic may become difficult. On the other hand, if the pore size thereof exceeds 3,000 μm, the cosmetic-supporting capability may deteriorate.

The pore number of the reticulated porous foam preferably falls in the range of 5 to 500 ppi (part per inch), and more preferably 20 to 200 ppi. The density of the reticulated porous foam preferably falls in the range of 0.01 to 0.5 g/cm$^3$, and more preferably 0.01 to 0.2 kg/cm$^3$, and may be appropriately adjusted depending on the composition of the cosmetic.

In the cosmetic-supporting structure according to the present invention, the hardness of the reticulated porous foam preferably falls in the range of 0.5 to 15 kPa (CLD (Compression Load Deflection) @25%), and more preferably 2 to 10 kPa. If the hardness of the foam is less than 0.5 kPa, the amount of the cosmetic that is discharged using a makeup tool such as a puff may become excessive. On the other hand, if the hardness thereof exceeds 15 kPa, it is difficult to discharge the cosmetic.

The hardness of the cosmetic-supporting structure according to the present invention preferably falls in the range of 2 to 15 kPa (CLD (Compression Load Deflection) @25%), and more preferably 3 to 9 kPa. If the hardness of the foam is less than 2 kPa, the amount of the cosmetic that is discharged using a makeup tool such as a puff may become excessive. On the other hand, if the hardness thereof exceeds 15 kPa, it is difficult to discharge the cosmetic, and the tactile sensation may decrease.

A reticulated porous architecture of the foam is configured such that many small pores are formed on the inside or the surface thereof, and the shape and number of the pores may vary depending on the type of cosmetic composition, and the architecture of the foam may vary depending on the portions thereof. For example, the reticulated porous architecture may have a three-dimensional reticulated shape, an open cell shape, etc.

The foam may be manufactured by foaming a specific polymer resin. Also, pores may be formed by adding a specific material, followed by dissolving it or removing the corresponding material through a chemical reaction, etc. Moreover, pores may be formed in a manner in which the resin is processed in the form of a nonwoven fabric or in which a particulate resin is sintered. The present invention is not particularly limited thereto, and pores may be manufactured through any process known in the art.

When the foam is manufactured through the foaming process, the pore size and porosity of the foam and the distribution and density of pores may be adjusted depending on the end use by controlling the foaming process. Typically, the foaming process may be conducted while appropriately adjusting the amount and kind of a foaming agent, the kind and supply amount of foaming gas, the foaming temperature and pressure, and other additives, as will be apparent to those skilled in the art.

The reticulated porous foam may be formed of a material including at least one selected from the group consisting of a polyetherester elastomer, polyurethane, NBR (AcryloNitrile-Butadiene Rubber), SBR (Styrene Butadiene Rubber), NR (Natural Rubber), BR (Butadiene Rubber), polyvinyl chloride, polyethylene, EVA (Ethylene Vinyl Acetate), latex, film type, SIS (Styrene Isoprene Styrene), SEBS (Styrene Ethylene Butylene Styrene), PVA (PolyVinyl Alcohol), PLA (Polylactic acid), a silicone elastomer, nitrile, butyl, polyether, and neoprene.

For example, the material for the foam may be composed exclusively of a polyetherester elastomer, or may include a mixture of polyetherester elastomer and polyurethane. The polymer resin may include an additive such as an antimicrobial material. Examples of the antimicrobial material may include urushiol, cardanol, castor oil-derived polyol, ionized gold, silver, and the like.

The polyetherester elastomer resin, which is an example of the material for the foam, is not limited, so long as it has elastomer properties by being composed of a hard segment containing a diol and a dicarboxylate (or dicarboxylic acid) and a soft segment containing a polyol and a dicarboxylate (or dicarboxylic acid). Specifically, as a polyetherester elastomer resin comprising a hard segment of butanediol and dimethyl terephthalate and a soft segment of polyether-based polyol and dimethyl terephthalate, a polyetherester elastomer resin having high molecular weight may be prepared by subjecting a dicarboxylate (or dicarboxylic acid) and diol and polyol to first transesterification (or esterification) and then to polycondensation in a separate reactor. The kinds of diol and polyol are not particularly limited, and may be used alone or in combination. Examples of the dicarboxylate (or dicarboxylic acid) may include dimethyl terephthalate, terephthalic acid, dimethyl isophthalate, isophthalic acid, dimethyl naphthalate, naphthalene dicarboxylic acid, adipic acid, azelaic acid and sebacic acid, examples of the diol may include butanediol (butylene glycol), monoethylene glycol, diethylene glycol, propylene glycol and neopentyl glycol, and examples of the polyol may include polytetramethylene glycol, polyethylene glycol, and polypropylene glycol.

As an example of the material for the foam, polyurethane includes polyether-based urethane and polyester-based urethane. The polyester-based urethane is not preferable because chemical resistance may be further decreased due to decomposition through a reaction such as hydrolysis upon cosmetic supporting, but in the present invention, the polyester-based urethane foam is improved in chemical resistance, durability, etc. through silicone resin coating, and may thus be appropriately used for cosmetic supporting.

In the cosmetic-supporting structure according to the present invention, the silicone coating layer may be formed of a coating composition including, based on the total weight of the composition, 70 to 100 wt % of a silicone compound and 0 to 30 wt % of an organic solvent, and preferably a coating composition including 100 wt % of a silicone compound.

The coating composition may further include at least one selected from the group consisting of a colorant, a filler, a plasticizer, and an antimicrobial agent. In the cosmetic-supporting structure according to the present invention, the coating composition may be cured at 100 to 220° C. for 5 to 60 min, and preferably at 120 to 200° C. for 10 to 30 min.

The hardness of the coating composition preferably falls in the range of 5 to 80 using a Shore A hardness meter, and more preferably 10 to 50. If the hardness thereof falls outside of the above range, the hardness of the cosmetic-supporting structure may become too low or high.

The viscosity of the coating composition at 25° C. preferably falls in the range of 10,000 to 800,000 cps, and more preferably 10,000 to 200,000 cps. If the viscosity thereof falls outside of the above range, it is difficult to form a desired coating layer or to efficiently perform a coating process.

The viscosity thereof may be adjusted by altering the components of the silicone coating composition or by altering the amount of the organic solvent, but the present invention is not limited thereto.

The hardness of the silicone compound may vary depending on the kind and end use of the cosmetic composition.

The silicone compound may be a compound containing a siloxane (Si—O—Si) group. The compound containing a siloxane group may include, but is not particularly limited to, dimethyl polysiloxane, methylhydrogen polysiloxane, or methylphenyl polysiloxane.

The organic solvent may include, but is not particularly limited to, a hydrocarbon, such as xylene, benzene, toluene, etc.; a lower alcohol, such as ethanol, methanol, isopropanol, etc.; a ketone, such as acetone, methyl ethyl ketone, etc.; a lower fatty acid ester, such as methyl acetate, ethyl acetate, butyl acetate, etc.; and an ether, such as methyl ether, ethyl ether, tetrahydrofuran, dioxane, etc.

In the cosmetic-supporting structure according to the present invention, at least one of the reticulated porous foam and the silicone coating layer may further include an antimicrobial agent. The antimicrobial agent is not particularly limited, and any component known in the art may be used.

In the cosmetic-supporting structure according to the present invention, the cosmetic may include at least one selected from the group consisting of a UV screen, an oil component, a surfactant, an aqueous component, an emulsion stabilizer, and an alcohol.

In the present invention, a silicone resin coating layer may be manufactured by immersing the foam in the silicone coating composition for a predetermined period of time, followed by squeezing and curing. Also, the coating process may be carried out by spraying the silicone coating composition onto the foam.

In order for the foam containing the silicone resin to have properties (e.g. hardness) suitable for end uses such as cosmetic supporting, coating, and the like, the properties of the foam before immersion in the silicone solution and the properties of the silicone resin may be selectively adjusted. For example, in order for the foam containing the silicone resin to have hardness suitable for cosmetic supporting, a foam having lower hardness may be used as the foam before immersion in silicone, thereby manufacturing a foam having appropriate hardness after final impregnation.

The immersion process is one in which the surface and the inside of the foam are uniformly coated with the silicone solution. The immersion process may be conducted through any process known in the art. For example, the surface and the inside of the foam may be coated with the silicon solution by placing the foam in the silicone coating composition for a predetermined period of time. Also, the surface and the inside of the foam may be more uniformly and rapidly coated with the silicon solution by placing the foam in the silicone coating composition and repeatedly performing pressurization and depressurization.

Also, the immersion process may be performed in a manner in which the silicone composition is injected into the foam. Specifically, the silicone coating composition is injected into the foam via a single injection pipe or multiple injection pipes, thereby uniformly coating the surface and the inside of the foam with the silicone solution. The immersion process through injection using the injection pipe is advantageous because more uniform and rapid coating of the center of the foam with the silicone coating composition becomes possible and because the amount of the silicone coating composition necessary for the immersion may be reduced. Also, pressure is applied to the foam before injection of the silicone coating composition, and thus the foam is pressurized, after which the silicone coating composition is injected into the foam via single or multiple injection pipes in coincidence with gradually depressurizing the foam, whereby the surface and the inside of the foam may be more uniformly and rapidly coated with the silicone coating composition. Furthermore, when the injection of the silicone coating composition into the foam is performed, suction of air around the foam may be simultaneously performed. In this case, the silicone solution injected into the foam via the injection pipe may be more efficiently applied in a more uniform and rapid manner on the surface and the inside of the foam through the flow of sucked air.

These immersion processes may be performed alone or in coincidence with each other.

The squeezing process is one in which a predetermined amount of solution is removed through appropriate pressurization of the foam or suction under reduced pressure and the thickness of the silicone coating composition evenly applied on the surface and inside of the foam is appropriately adjusted depending on the end use and the properties required therefor. The squeezing process may be performed using a press roller or a vacuum suction machine, but any tool or machine may be used without limitation so long as it enables pressurization or suction under reduced pressure. The pressurization or suction under reduced pressure may be conducted about 1 to 3 times, but the present invention is not particularly limited thereto.

The curing process is one in which a liquid silicone composition is cured into a solid. While the liquid silicone composition is cured through the curing process, a solid coating layer around the foam frame is formed, thus manufacturing a cosmetic-supporting structure having a silicone coating layer. The curing process may be conducted through any process known to those skilled in the art, and for example, may be performed by allowing the foam to stand in a hot-air oven at 100° C. or more for 10 min.

The cosmetic-supporting structure may be used to support a cosmetic, and functions to support and store a cosmetic before use by the user and then to discharge an appropriate amount of the cosmetic so as to be applied on the skin when used by the user. Here, the foam for cosmetic supporting may be smeared on a makeup tool (e.g. a puff) and thus applied on the skin, or may be brought into direct contact with the skin and thus applied thereon without the use of an additional makeup tool. Briefly, the foam for cosmetic supporting requires chemical resistance, durability, charging capability, supporting capability, and discharging capability.

The cosmetic may be a water-in-oil-type cosmetic composition in which water as an inner phase is dispersed in oil as an outer phase. As the oil-to-water ratio is adjusted, properties such as viscosity may be controlled, and also the extent of supporting on the porous foam, the extent of discharge upon pressurization, etc. may be regulated. However, in the present invention, not only the water-in-oil-type cosmetic but also oil-in-water-type, soluble-type, and oil-type cosmetics may be used, depending on the viscosity.

The cosmetic composition include an oil component (oil), a surfactant, an aqueous component, an emulsion stabilizer, an alcohol, and a UV screen, and may also include an animal/vegetable extract, such as a licorice extract, a green tea extract, etc., an enzyme such as lipase, and an organic acid such as lactic acid, glycolic acid, etc.

The UV screen may be an organic UV screen, and may include, but is not particularly limited to, any one or a mixture of two or more selected from among glyceryl para-aminobenzoic acid (PABA), drometrizole, digalloyl trioleate, 3-(4-methylbenzylidene)-camphor, methyl anthranilate, bis-ethylhexyloxyphenol methoxyphenyl triazine, diethylamino hydroxybenzoyl hexyl benzoate, benzophenone-3, benzophenone-4, benzophenone-8, butylmethoxy dibenzoylmethane, cinoxate, ethylhexyl triazone, ethylhexyl methoxycinnamate, octocrylene, octyldimethyl PABA, octyl salicylate, oxybenzone, cinoxate, octyl triazone, ethylhexyl salicylate, para-aminobenzoic acid, 2-phenylbenzimidazole-5-sulfonic acid, homosalate, isoamyl-p-methoxycinnamate, bis-ethylhexyloxyphenol methoxyphenyl triazine, drometrizole trisiloxane, and polysilicone-15.

The oil component may include, but is not limited to, any one or a mixture of two or more selected from among vegetable oils such as avocado oil, jojoba oil, camellia oil, olive oil, rosehip oil, safflower oil, peach seed oil, meadowfoam seed oil, sunflower seed oil and jojoba oil, animal oils such as squalane, mink oil, and horse oil, synthetic esters or hydrocarbons such as dicaprylyl carbonate, neopentyl glycol diheptanoate, tocopheryl acetate, trioctanoin, C12-15 alkyl benzoate, C12-15 alkylethyl hexanoate, octyldodecyl myristate, tricaprylin, octyl dodecylstearoyl stearate, bis-hydroxyethoxypropyl dimethicone, caprylic/capric triglyceride, isotridecyl isononanoate, polyglyceryl-2-triisostearate, diisostearyl maleate, dipentaerythrite fatty acid ester, cetyl octanoate, and ozocerite, higher fatty acids such as lauric acid, myristic acid, palmitic acid, and stearic acid, higher alcohols such as cetyl alcohol, cetearyl alcohol, and stearyl alcohol, and silicone oil such as phenyl trimethicone, cyclomethicone, dimethicone, and decamethylcyclopentasiloxane.

The surfactant may include, but is not limited to, any one or a mixture of two or more selected from among cyclopentasiloxane and PEG/PPG-18/18 dimethicone, glycol stearate, sorbitan sesquioleate, glyceryl oleate, glycol distearate, propylene glycol monostearate, glyceryl stearate, sorbitan stearate, polysorbate 20, polysorbate 60, PEG-30 dipolyhydroxystearate, PEG-10 dimethicone, cyclopentasiloxane/PEG.PPG-19.19 dimethicone, sorbitan isostearate, lauryl PEG.PPG-18.18 methicone, cetyl PEG.PPG-10.1 dimethicone, lauryl PEG-9 polydimethylsiloxyethyl dimethicone, lauryl alcohol, cetyl alcohol, lecithin, saponin, sugar ester, glycolipids, and wax.

The emulsion stabilizer may include, but is not limited to, any one or a mixture of two or more selected from among sodium chloride and magnesium sulfate.

The alcohol may include, but is not limited to, any one or a mixture of two or more selected from among ethanol, benzyl alcohol, and phenoxyethanol.

The aqueous component may include, but is not limited to, any one or a mixture of two or more selected from among purified water, 1,3-butyleneglycol, glycerin, and propylene glycol.

The cosmetic-supporting structure may be used to apply a cosmetic, which means that the cosmetic composition is applied on the skin of a user upon use, specifically, that a cosmetic is transferred to the skin by bringing a makeup tool on which the cosmetic is smeared into contact with the skin.

In addition, the present invention addresses a cosmetic product including the cosmetic-supporting structure.

The cosmetic composition may be provided in the form of any formulation, such as a makeup primer, a makeup base, a foundation, a skin cover, a lipstick, a lip-gloss, a face powder, a lip liner pencil, an eyebrow pencil, an eyeshadow, a cheek color, a compact powder, a twin cake, a compact, a powder compact, an eyeliner, an eyeshadow, a concealer, a blush, a powder foundation, a lotion, a skin toner, or an airless formulation, but the present invention is not limited thereto.

Although a cosmetic composition is difficult to carry and store in a liquid phase, rather than in a solid phase, the use of the cosmetic product including the cosmetic-supporting structure according to the present invention is preferable because the cosmetic composition in a liquid phase or a cream phase may be stored and carried stably and safely. When the cosmetic composition is in a solid phase, it is supported on the cosmetic-supporting structure to thus reduce rapid changes in properties of the solid due to external shocks such as impact or heat. Furthermore, when the cosmetic is used, the cosmetic-supporting structure functions to fix the cosmetic, whereby the cosmetic may be discharged only in an appropriate amount.

In addition, the present invention addresses a method of manufacturing the cosmetic-supporting structure, comprising: forming a silicone coating layer, serving as an outer frame, on the outer surface of a reticulated porous foam, serving as an inner frame.

The method of the invention includes immersing the reticulated porous foam in a silicone coating composition, squeezing the foam through pressurization, and curing the foam, a detailed description of which remains the same as in the foregoing.

MODE FOR INVENTION

A better understanding of the present invention will be given through the following examples, which are merely set forth to illustrate, but are not to be construed as limiting the present invention, and the present invention may be variously modified and altered.

Preparation Example 1-1: Preparation of Polyurethane Foam

A polyurethane foam was manufactured through a typical process using a composition comprising 100 g of polyester polyol (HP-3193, made by Heungil Polychem), 62.7 g of toluene diisocyanate (TDI-80, made by KPX Fine Chemical), 2.0 g of a silicone surfactant (TEGOSTAB B-8404, made by Goldschmidt), 2 g of a first foaming agent (water), 11.5 g of a second foaming agent (HFC365mfc/227ea, made by Inventec), 0.05 g of a first amine catalyst (NIAX A-1, made by Momentive), and 0.15 g of a second amine catalyst (Dabco D-33LV, made by Air Product). The polyurethane foam had an average pore size of 400 μm and a hardness of 3 kPa.

Preparation Example 1-2: Preparation of Polyurethane Foam

A polyurethane foam having an average pore size of 400 μm and a hardness of 16 kPa was manufactured using the same composition as in Preparation Example 1-1.

Preparation Example 1-3: Preparation of Polyurethane Foam

A polyurethane foam having an average pore size of 25 μm and a hardness of 3 kPa was manufactured using the same composition as in Preparation Example 1-1.

Preparation Example 1-4: Preparation of Polyetherester Elastomer Resin Foam

Dimethyl terephthalate, butanediol, and polytetramethylene glycol constituting a soft segment of an elastomer were placed in a transesterification reactor, after which tetrabutoxy titanate (TBT) was added as a transesterification catalyst and a transesterification reaction was carried out while the temperature was elevated.

After termination of the transesterification reaction, the prepared oligomer was uniformly added with tetrabutoxy titanate (TBT) as a polycondensation catalyst and then transferred into a polycondensation reactor using a transfer pipe. When the prepolymer was transferred, N,N'-hexane-1,6-diyl bis(3-(3,5-di-tert-butyl-4-hydroxyphenyl-propionamide)) and N,N'-trimethylenebis-(3-3,5-di-t-butyl-4-hydroxyphenyl)propionamide) antioxidants were dispersed in butanediol and thus added thereto using an injection device.

The prepolymer mixture transferred into the polycondensation reactor was depressurized stepwise so that a polycondensation reaction was progressed, thereby preparing a polyetherester elastomer resin.

Thereafter, the polyetherester elastomer resin was foamed through a process typically known in the art, resulting in a foam having a pore size of 350 μm and hardness of 3.5 kPa.

Preparation Example 2-1: Preparation of Silicone Coating Composition

As a silicone coating composition, a two-component liquid silicone resin (trade name: LSI-280/30, made by HRS, hardness: Shore A 30) containing polydimethylsiloxane was prepared.

Preparation Example 2-2: Preparation of Silicone Coating Composition

As a silicone coating composition, a two-component liquid silicone resin (trade name: LSI-280/70, made by HRS, hardness: Shore A 70) containing polydimethylsiloxane was prepared.

Example 1: Formation of Silicone Resin-Coated Foam

The polyurethane foam (ether foam, average pore size: 400 μm) of Preparation Example 1-1 was immersed in the silicone coating composition of Preparation Example 2-1, squeezed through appropriate pressurization and then cured, thus manufacturing a silicone resin-coated foam.

The weight ratio of the silicone resin-coated foam and the silicone coating layer was 0.3:0.7 (1:2.4), and the thickness of the silicone coating layer was 10 μm to 20 μm.

Example 2: Formation of Silicone Resin-Coated Foam

The polyurethane foam (ether foam, average pore size: 400 μm) of Preparation Example 1-1 was immersed in the silicone coating composition of Preparation Example 2-1, squeezed through appropriate pressurization and then cured, thus manufacturing a silicone resin-coated foam.

The weight ratio of the silicone resin-coated foam and the silicone coating layer was 0.81:0.19 (1:0.23), and the thickness of the silicone coating layer was 0.8 μm to 0.9 μm.

Example 3: Formation of Silicone Resin-Coated Foam

The polyurethane foam (ether foam, average pore size: 400 μm) of Preparation Example 1-1 was immersed in the silicone coating composition of Preparation Example 2-2, squeezed through appropriate pressurization and then cured, thus manufacturing a silicone resin-coated foam.

The weight ratio of the foam and the silicone coating layer was 0.3:0.7 (1:2.33), and the thickness of the silicone coating layer was 10 μm to 25 μm. The hardness of the foam was 17 kPa.

Example 4: Formation of Silicone Resin-Coated Foam

The polyurethane foam (ether foam, average pore size: 400 μm) of Preparation Example 1-2 was immersed in the silicone coating composition of Preparation Example 2-1, squeezed through appropriate pressurization and then cured, thus manufacturing a silicone resin-coated foam.

The weight ratio of the foam and the silicone coating layer was 0.3:0.7 (1:2.33), and the thickness of the silicone coating layer was 10 μm to 25 μm. The hardness of the foam was 18 kPa.

Example 5: Formation of Silicone Resin-Coated Foam

The polyurethane foam (ether foam, average pore size: 25 μm) of Preparation Example 1-3 was immersed in the silicone coating composition of Preparation Example 2-1, squeezed through appropriate pressurization and then cured, thus manufacturing a silicone resin-coated foam.

The weight ratio of the foam and the silicone coating layer was 0.5:0.5 (1:1), and the thickness of the silicone coating layer was 6 μm to 12 μm.

Example 6: Formation of Silicone Resin-Coated Foam

A polyurethane foam B (ether foam, average pore size: 400 μm) was immersed in the silicone coating composition of Preparation Example 2-1, squeezed through appropriate pressurization and then cured, thus manufacturing a silicone resin-coated foam.

The weight ratio of the silicone resin-coated foam and the silicone coating layer was 0.3:0.7 (1:2.4), and the thickness of the silicone coating layer was 10 μm to 20 μm.

Example 7: Formation of Silicone Resin-Coated Foam

A polyurethane foam E (ester foam, average pore size: 300 μm) was immersed in the silicone coating composition of Preparation Example 2-1, squeezed through appropriate pressurization and then cured, thus manufacturing a silicone resin-coated foam.

The weight ratio of the silicone resin-coated foam and the silicone coating layer was 0.3:0.7 (1:2.4), and the thickness of the silicone coating layer was 10 μm to 20 μm.

Example 8: Formation of Silicone Resin-Coated Foam

The polyetherester elastomer resin foam (average pore size: 350 μm) of Preparation Example 1-4 was immersed in the silicone coating composition of Preparation Example 2-1, squeezed through appropriate pressurization and then cured, thus manufacturing a silicone resin-coated foam.

The weight ratio of the silicone resin-coated foam and the silicone coating layer was 0.3:0.7 (1:2.4), and the thickness of the silicone coating layer was 10 μm to 20 μm.

Test Example 1. Evaluation of Properties of Silicone Resin-Coated Foam

Useful as a UV screen, ethylhexyl methoxycinnamate (also called octyl methoxycinnamate or octinoxate) was supported in an amount of 0.8 g for 1 $cm^3$ of foam volume on the silicone resin-coated foam of each of Examples 1 to 8 and stored at 60° C. for 48 hr, and a swelling ratio based on changes in the size of the upper surface thereof was measured. 10 days after storage, the extent of deformation of the foam and changes in hardness thereof were measured. The results thereof are shown in Table 1 below.

In Comparative Examples, reticulated porous foams made of polyurethane, NBR (AcryloNitrile-Butadiene Rubber), SBR (Styrene Butadiene Rubber), NR/SBR (Natural Rubber/Styrene Butadiene Rubber), and polyetherester elastomer resin, which are conventionally used for cosmetic supporting or coating, were used.

TABLE 1

| Foam material | Swelling ratio (%) | Deformation (Distortion) | Hardness | Amount of discharged cosmetic | Tactile sensation |
|---|---|---|---|---|---|
| Silicone-containing polyurethane foam (Preparation Example 1-1, ester type, Example 1) | 11.4 | −/+ | −/+ | ○ | ⊚ |
| Silicone-containing polyurethane foam (Preparation Example 1-1, ester type, Example 2) | 12.8 | + | + | ○ | ○ |
| Silicone-containing polyurethane foam (Preparation Example 1-1, ester type, Example 3) | 11.6 | −/+ | −/+ | ∇ | △ |
| Silicone-containing polyurethane foam (Preparation Example 1-2, ester type, Example 4) | 11.9 | −/+ | −/+ | ∇ | △ |
| Silicone-containing polyurethane foam (Preparation Example 1-3, ester type, Example 5) | 11.8 | −/+ | −/+ | ∇ | ○ |
| Silicone-containing polyurethane foam B (ether type, Example 6) | 14.1 | −/+ | −/+ | ○ | ⊚ |
| Silicone-containing polyurethane foam E (ester type, Example 7) | 10.9 | −/+ | −/+ | ○ | ⊚ |
| Polyetherester elastomer resin foam (Example 8) | 12.1 | −/+ | −/+ | ○ | ○ |
| Polyurethane foam A1 (ether type, Comparative Example 1) | 37.2 | ++ | +++ | ○ | △ |
| Polyurethane foam B (ether type, Comparative Example 2) | 39.4 | ++ | +++ | ○ | △ |
| Polyurethane foam C (ether type, Comparative Example 3) | 35.6 | ++ | +++ | ○ | △ |
| Polyurethane foam D (ester type, Comparative Example 4) | 16.4 | ++ | ++ | ○ | △ |
| Polyurethane foam E (ester type, Comparative Example 5) | 16.8 | ++ | ++ | ○ | △ |
| Polyurethane foam F (ester type, Comparative Example 6) | 19.5 | ++ | ++ | ○ | △ |
| NBR (Comparative Example 7) | 86.4 | +++ | +++ | △ | ∇ |
| SBR (Comparative Example 8) | 122.6 | +++ | +++ | △ | ∇ |

TABLE 1-continued

| Foam material | Swelling ratio (%) | Deformation (Distortion) | Hardness | Amount of discharged cosmetic | Tactile sensation |
|---|---|---|---|---|---|
| NR/SBR (Comparative Example 9) | 72.7 | +++ | +++ | Δ | ∇ |
| Polyetherester elastomer resin foam of Preparation Example 1-5 (Comparative Example 10) | 15.1 | ++ | ++ | ○ | Δ |

Note)
Polyurethane foam B: Manufacturer/Purchaser Polytech, ether type, 60 ppi
Polyurethane foam C: Manufacturer/Purchaser Foamtech, ether type 80 ppi
Polyurethane foam D: Manufacturer/Purchaser Polytech, ester type, 60 ppi
Polyurethane foam E: Manufacturer/Purchaser made in Germany, ester type, 80 ppi
Polyurethane foam F: Manufacturer/Purchaser made in Japan, ester type, 80 ppi
NBR: Manufacturer/Purchaser Aritaum
SBR: Manufacturer/Purchaser Aritaum
NR/SBR: Manufacturer/Purchaser Aritaum As is apparent from Table 1, the swelling ratio was calculated using Equation 1 below. The results of Table 1 show the results after supporting the cosmetic composition on the foam, and the evaluation criteria for deformation and hardness were as follows:

$$\text{Swelling ratio (\%)} = \{(\text{area of upper surface of foam after supporting of ethylhexyl methoxycinnamate} - \text{area of upper surface of foam before supporting of ethylhexyl methoxycinnamate}) / \text{area of upper surface of foam before supporting of ethylhexyl methoxycinnamate}\} \times 100 \quad [\text{Equation 1}]$$

<Evaluation Criteria for Deformation>
−/+: Almost no change
+: Slight deformation
++: Deformation
+++: Severe deformation <Evaluation Criteria for Hardness>
−/+: Almost no change
+: Slight reduction
++: Reduction
+++: Severe reduction In Table 1, the evaluation of the amount of cosmetic that was discharged was performed through blind tests by 10 females in their twenties as subjects. Specifically, the amounts discharged through the puffs in the state in which the cosmetic compositions of Table 2 below were contained in the foams of Examples and Comparative Examples were measured by the subjects, and the results thereof were expressed in numerical points from 1 to 5, and the numerical points thereof were averaged and evaluated based on the following criteria.

Evaluation Criteria for Amount of Discharged Cosmetic

○: Good
Δ: Excess
∇: Poor

As is apparent from Table 1, the tactile sensation was evaluated through blind tests by 10 females in their twenties as subjects. Specifically, the tactile sensations through the puffs in the state in which the cosmetic compositions of Table 2 below were contained in the foams of Examples and Comparative Examples were measured by the subjects, and the results thereof were expressed in numerical points from 1 to 5, and the numerical points thereof were averaged and evaluated based on the following criteria.

<Evaluation Criteria for Tactile Sensation>
⊚: 4.1 to 5 (Very good)
○: 3.1 to 4 (Good)
Δ: 2.1 to 3 (Poor)
×: 1.1 to 2 (Very poor)

TABLE 2

| Classification | Raw material | wt % |
|---|---|---|
| Oil component | Cyclopentasiloxane | 16.0 |
| | Phenyl trimethicone | 11.0 |
| | Caprylic/capric triglyceride | 4.0 |
| | Ethylhexyl methoxycinnamate | 7.0 |
| | PEG-10 dimethicone | 3.0 |
| | Sorbitan sesquioleate | 1.0 |
| | Ethylhexyl salicylate | 3.0 |
| Thickener | Disteardimonium hectorite | 0.3 |
| Pigment | Titanium dioxide | 10.0 |
| | Iron oxide | 1.2 |
| | Zinc oxide | 5.0 |
| Aqueous component | Purified water | Remainder |
| | Dipropylene glycol | 5.0 |
| | Sodium chloride | 1.0 |
| | Glycerin | 2.5 |
| | Phenoxyethanol | 0.3 |

As is apparent from Table 1, the silicone-coated foams of Examples 1 to 8 were superior in deformation resistance and chemical resistance to a UV screen component (ethylhexyl methoxycinnamate) compared to Comparative Examples 1 to 10. Also, superior cosmetic retention and tactile sensation were exhibited. Specifically, swelling and deformation of the foams of Comparative Examples 1 to 10 were significant when supported with a UV screen component (ethylhexyl methoxycinnamate), whereas the foams of Examples 1 to 8 were little deformed and the swelling ratio thereof was very low. Furthermore, a reduction in hardness was lower in Examples 1 to 8 than in Comparative Examples 1 to 10, from which the initial hardness was confirmed to be maintained upon use for cosmetic supporting.

According to the present invention, the silicone-coated cosmetic-supporting structure has effects of high deformation resistance and chemical resistance to the cosmetic composition, including not only the UV screen but an oil component (oil), an aqueous component, a surfactant, an emulsion stabilizer, and an alcohol.

In addition, the cosmetic was supported on the silicone-containing ester-based polyurethane foam E of Example 7 and the silicone-free ester-based polyurethane foam E (Comparative Example 5) and then stored for 40 days at 60° C., and foam changes were observed. The results are shown in FIG. 1.

As results thereof, the silicone-containing ester-based polyurethane foam was not deformed even after 40 days, but the shape thereof was maintained, whereas the silicone-free ester-based polyurethane foam was decomposed and the structure thereof was broken.

Therefore, the cosmetic-supporting structure according to the present invention has effects of high deformation resistance and chemical resistance to the cosmetic composition, including a UV screen, an oil component (oil), an aqueous component, a surfactant, an emulsion stabilizer, and an alcohol.

The invention claimed is:

1. A cosmetic-supporting structure, comprising:
   a reticulated porous foam; and
   a silicone coating layer, serving as an outer frame, on an outer surface of the foam, serving as an inner frame,
   wherein a pore size of the reticulated porous foam is 400 μm to 3,000 μm,
   wherein the silicone coating layer is formed of a silicone-containing coating composition that has a viscosity of 10,000 to 800,000 cps at 25° C.,
   wherein a Shore A hardness of the coating composition upon curing is 10 to 50,
   wherein a weight ratio of the reticulated porous foam and the silicone coating layer is 1:0.5 to 1:7, and
   wherein a thickness of the silicone coating layer is 1 μm to 25 μm.

2. The cosmetic-supporting structure of claim 1, wherein a hardness of the cosmetic-supporting structure is 2 to 15 kPa.

3. The cosmetic-supporting structure of claim 1, wherein a hardness of the reticulated porous foam is 0.5 to 15 kPa.

4. The cosmetic-supporting structure of claim 1, wherein the reticulated porous foam is formed of a material including at least one selected from the group consisting of a polyetherester elastomer, polyurethane, NBR (AcryloNitrile-Butadiene Rubber), SBR (Styrene Butadiene Rubber), NR (Natural Rubber), BR (Butadiene Rubber), polyvinyl chloride, polyethylene, EVA (Ethylene Vinyl Acetate), latex, film type, SIS (Styrene Isoprene Styrene), SEBS (Styrene Ethylene Butylene Styrene), PVA (PolyVinyl Alcohol), PLA (Polylactic acid), a silicone elastomer, nitrile, butyl, polyether, and neoprene.

5. The cosmetic-supporting structure of claim 1, wherein the silicone coating layer is formed using a coating composition comprising 70 to 100 wt % of a silicone compound and 0 to 30 wt % of an organic solvent based on a total weight of the composition.

6. The cosmetic-supporting structure of claim 5, wherein the coating composition further comprises at least one selected from the group consisting of a pigment, a filler, a plasticizer, a catalyst, and an antimicrobial agent.

7. The cosmetic-supporting structure of claim 5, wherein the coating composition is cured within 5 min to 60 min.

8. The cosmetic-supporting structure of claim 5, wherein the silicone compound is a compound containing a siloxane (Si—O—Si) group.

9. The cosmetic-supporting structure of claim 1, wherein at least one of the reticulated porous foam and the silicone coating layer further comprises at least one selected from the group consisting of a pigment, a filler, a plasticizer, a catalyst, and an antimicrobial agent.

10. The cosmetic-supporting structure of claim 1, wherein the cosmetic comprises at least one selected from the group consisting of a UV screen, an oil component, a surfactant, an aqueous component, an emulsion stabilizer, and an alcohol.

11. A cosmetic product, comprising the cosmetic-supporting structure of claim 1.

12. The cosmetic-supporting structure of claim 1, wherein the silicone coating layer is thermal curing layer.

13. The cosmetic-supporting structure of claim 1, wherein the pore size of the reticulated porous foam is 499-400 μm to 1,000 μm.

14. A method of manufacturing a cosmetic-supporting structure of claim 1, comprising:
    forming a silicone coating layer from a silicone-containing coating composition on an outer surface of a reticulated porous foam,
    wherein the silicone coating layer serves as an outer frame,
    wherein the reticulated porous foam serves as an inner frame,
    wherein a pore size of the reticulated porous foam is 400 μm to 3,000 μm,
    wherein a viscosity of the silicone-containing coating composition is 10,000 to 800,000 cps at 25° C.,
    wherein a Shore A hardness of the coating composition upon curing is 10 to 50,
    wherein a weight ratio of the reticulated porous foam and the silicone coating layer is 1:0.5 to 1:7, and
    wherein a thickness of the silicone coating layer is 1 μm to 25 μm.

15. The method of claim 14, comprising:
    immersing the reticulated porous foam in a silicone coating composition;
    squeezing the foam through pressurization; and
    curing the foam.

16. The method of claim 15, wherein the curing the foam is performed through thermal curing.

* * * * *